United States Patent [19]

Wulff et al.

[11] Patent Number: 5,696,295
[45] Date of Patent: Dec. 9, 1997

[54] METHOD FOR THE PREPARATION OF ULTRA-PURE BISPHENOL A AND THE USE THEREOF

[75] Inventors: Claus Wulff, Krefeld; Kaspar Hallenberger; Heinrich Steude, both of Leverkusen, all of Germany; Kurt-Peter Meurer, Antwerp, Belgium; Tony van Osselaer, St.-Niklaas/Belsele, Belgium; Jürgen Hinz, Brasschaat, Belgium; Frank Quaeyhaegens, Mortsel, Belgium; Johan Vaes, Kaltmhout, Belgium; Ignace Hooftman, Kruibeke, Belgium

[73] Assignee: Bayer AG, Leverkusen, Germany

[21] Appl. No.: 418,583

[22] Filed: Apr. 6, 1995

[30] Foreign Application Priority Data

Apr. 18, 1994 [DE] Germany ............... 44 13 396.0

[51] Int. Cl.[6] .............. C07C 37/74; C07C 39/12; C07C 39/16
[52] U.S. Cl. .............. 568/724; 568/722; 568/723
[58] Field of Search .................. 568/722, 724, 568/723

[56] References Cited

U.S. PATENT DOCUMENTS

| 5,198,591 | 3/1993 | Kiedik et al. ............ 568/727 |
| 5,269,887 | 12/1993 | Jakob et al. ............ 568/724 |

FOREIGN PATENT DOCUMENTS

| 738962 | 3/1970 | Belgium ............ 568/724 |
| 0 290 179 | 11/1988 | European Pat. Off. . |
| 0 499 922 | 8/1992 | European Pat. Off. . |
| 0 523 931 | 1/1993 | European Pat. Off. . |
| 0 567 855 | 11/1993 | European Pat. Off. . |

*Primary Examiner*—Jose G. Dees
*Assistant Examiner*—Rosalynd Williams
*Attorney, Agent, or Firm*—Connolly and Hutz

[57] ABSTRACT

The invention relates to a method for the purification by distillation of p,p-bisphenol A from the melt.

The p,p-bisphenol A melt thus obtained is highly heat-stable, stable in storage and colour-stable, is free from high-boiling components and no longer contains any surface-active or non-distillable metal, salt, acid or polymer components and no sulphur-containing components; o,p-BPA and phenol are removed and the low-boiling components are scarcely detectable.

2 Claims, No Drawings

METHOD FOR THE PREPARATION OF ULTRA-PURE BISPHENOL A AND THE USE THEREOF

The invention relates to a method for the preparation of ultra-pure bisphenol A (p,p-BPA content greater than 99.98%). High-boiling isomers such as Mol 402, trisphenol, spiroindane, indane etc., metals, metal dust, metal-/alkali-metal ions, salts, acidic components, oligomers, polymers, optionally functionalised, as well as surface-active compounds are removed.

Bisphenol A (BPA) is prepared, for example, from acetone and phenol in the presence of optionally modified ion-exchange resins according to known methods (for example, DE-A 3 727 641, corresponding to U.S. Pat. No. 4,912,263). Bisphenol A prepared in this way is suitable, without further purification, for use as a monomer unit for the preparation of other polymers, for example, polycarbonates.

However, if the polymers prepared from bisphenol A are to be of a particular purity and therefore to meet high requirements, bisphenol A which has already been produced in a high degree of purity must be further purified, for example, by crystallisation of a bisphenol A/phenol adduct and subsequent removal of the phenol (for example, DE-A 4 105 428, DE-A 4 213 872).

Bisphenol A which has been highly purified in this way has a purity of from 99.60 to 99.90% p,p-BPA content and a Hazen colour of 20 (flakes). The test (Hazen) measured at 166° C. for 1.5 hours gives a colour index of 50.

It has now been found that highly pure bisphenol A having a far superior colour index (Hazen 0–5) can be obtained if it is fractionated under vacuum and distilled, with the successive separation of high-boiling, low-boiling and undistilled components.

The invention provides a method for the preparation of ultra-pure bisphenol A, characterised in that (a) a bisphenol A melt, obtained by conventional processes for the preparation of BPA or by melting flakes, powder or pellets of BPA, having a p,p-bisphenol A content of at least 90% and phenol contents of less than 10%, is used as educt and distilled, (b) the distillation of this melt is carried out without 1.5 the addition of stabilizers and under inert conditions, (c) the distillation is carried out in such a way that the losses through decomposition of p,p-bisphenol A are less than 0.5%, (d) the distillation is carried out at temperatures of from 220° C. to 250° C., (f) the distillation takes place under vacuum at 1 to 50 mbar, (g) the distillation takes place in two stages, (h) first (h,1) high-boiling components such as Mol 402, indanes and trisphenols are completely removed, then (h,2) metal dust, metal ions and traces of salt, traces of acid, polymeric and oligomeric residues of catalysts and other non-distillable higher molecular compounds are completely removed, then (h, 3) surface-active compounds are completely removed, then (h,4) low-boiling components such as o,p-BPA, alkylphenols, traces of phenol as well as sulphur-containing low-boiling components such as mercaptopropionic acid are removed, then (h,5) concentrated BPA melt solutions containing low-boiling components, phenol and high-boiling components and having a p,p-bisphenol A content of greater than 92% are returned to the process as recycled streams, (i) not more than 5% of concentrated BPA melt solutions containing low-boiling components and not more than 10% of concentrated BPA melt solutions containing high-boiling components are channelled into the process, (j) low-boiling and high-boiling components contained in the channelled products mixed with p,p-BPA are returned to the process from the recycled streams, rearranged and partially recovered, (k) distilled p,p-bisphenol A is worked up in a conventional manner as a stable bottom product free of other substances.

The purified ultra-pure bisphenol A has a purity of greater than 99.98% p,p-bisphenol A content. Owing to the complete removal (less than 10 ppm) of the main impurity o,p-BPA, the high-boiling components and the non-distillable components from the BPA process, it has a thermocolour stability of as low as Hazen <5 in the melt and is distinguished by long-term heat stability (>200 hours) in the melt.

According to the invention previously purified BPA is used, with the preliminary purification of the bisphenol A being carried out firstly by the crystallisation of BPA-phenol adducts, then by filtration of the adducts and subsequent desorption of the phenol followed by the distillation of the BPA melt.

The distillation method is distinguished particularly in that the main impurity in the prepared bisphenol A, o,p-BPA, can be reduced to a content of less than 10 ppm. The low-boiling components are reduced to less than 150 ppm.

Highly pure distilled BPA according to the invention differs from highly pure crystallised BPA in that it is surface active in alkaline solutions, is particularly heat-stable and contains a proportion of o,p-BPA of less than 10 ppm. A solution of NaBPA which contains dissolved bisphenol A distilled according to the invention displays no foaming on being shaken or on the introduction of gas (for example, bubbling through of nitrogen) (high surface tension).

Bisphenol A which has been purified by fractional distillation is superior to bisphenol A obtained from solvents or phenol by conventional, large scale recrystallisation, in that the high-boiling components and the non-distillable components are completely removed, o,p-bisphenol A is removed to a content of less than 10 ppm and low-boiling components and phenol are removed to a content of less than 150 ppm.

The substances referred to as low-boiling components have a boiling point lower than that of bisphenol A (p,p-BPA: 220° C., 5 hPa) such as, for example, o,p-BPA, phenol, alkylated phenols, chromanes, etc. The substances referred to as high-boiling components have a boiling point higher than that of bisphenol A such as, for example, Mol 402, trisphenol, indane, spiroindane or other compounds having a molecular weight of greater than 300.

The p,p-bisphenol A purified according to the invention can C be stored as a liquid intermediate product for polymers which is transportable, capable of being stored at temperatures of above 160° C. and is heat-stable.

In the distillation according to the invention, bisphenol A having a content of at least 90% by weight of bisphenol A and less than 10% of isomers is fractionally distilled from the melt in a vacuum under inert gas. The distillation can be carried out in batches using a column supplied with a liquid separator or gas separator, or continuously by successive separation of high-boiling and low-boiling components by means of two technically designed columns.

The continuously operated two-column method under vacuum is carried out in such a way that first of all the high-boiling components, the non-distillable components and the components giving rise to instabilities (bottom of column 1) and then the low-boiling components are removed, with the advantage that any low-boiling components which may be formed in the bottom of the column from high-boiling components and bisphenol A by chemical rearrangement or decomposition processes can be removed at the top of column 2 together with the low-boiling components present in the educt.

The pressure is from 0.1 to 10 mbar; the temperature in the column bottoms is from 220° to 250° C.

In this way, sulphur-containing high-boiling components (oligomeric sulphates etc.), residues of mercaptopropionic acid and other sulphur-containing low-boiling components are removed from the bisphenol A.

The bisphenol A purified according to the invention has a content of up to 99.99% by weight of bisphenol A, less than 100 ppm of isomers and a Hazen colour of less than 5 (heat stability at 166° C.; 1.5 hours). The p,p-BPA thus purified is colour-stable for at least 20 hours at 230° C. and for at least 200 hours at 170° C.

A bisphenol A previously purified by crystallisation of the bisphenol A/phenol adducts and usable in the method according to the invention contains less than 10% of isomers and phenol.

The achieved result of high purity combined with the outstanding colour index, and in particular the removal of high-boiling and low-boiling isomers and non-distillable components of the bisphenol A melt prepared on a large scale, as well as the unexpectedly high thermocolour stability was not predictable, as it is generally known that bisphenol A undergoes decomposition and isomerises at elevated temperatures. Hitherto this has been regarded as a great disadvantage in the distillation of bisphenol A.

The composition of distilled bisphenol A is superior to that of bisphenols purified by other methods in that a very small proportion of o,p-BPA (less than 10 ppm) is present. This renders distilled bisphenol A of interest as a product for use in melt condensations. o,p-BPA is regarded as a chain stopper and colour-impairing component (tendency to decompose) in melt processes.

Highly pure bisphenol A obtained from solvents or phenol by one or more crystallisation stages differs from highly pure distilled bisphenol A in that, although the concentration of all the isomers occurring over the individual recrystallisation stages is reduced, they are always present—even though to a lesser extent—in the BPA melt (less than 1 ppm to 50 ppm for all the isomers)—and in particular o,p-bisphenol A (greater than 20 ppm), which is the main impurity of highly pure bisphenol A products commonly available on the market today.

Large-scale recrystallisation of bisphenol A is also technically more complicated and more costly than distillation. The considerable movements of solvent and the tank volumes required for the recrystallisation processes are further disadvantages. Furthermore crystallisation also has energy disadvantages.

Another advantage of distillation compared with discontinuous crystallisation, apart from the lower susceptibility to interference, is the continuous mode of operation. It makes possible a constancy of purity in the BPA melt, that is, the high colour stability and purity of the melt have the effect of improving the quality of the flakes or pellets as well as of the prepared sodium bisphenolate solutions, which in turn determine the constancy of quality for highly transparent, highly pure polymers (polycondensates).

A highly pure bisphenol A raw material also allows a reduction in the quantity of colour-stabilising additives required for colour-sensitive polymers such as for example certain types of polycarbonate.

A further advantage of highly pure distilled bisphenol A compared with highly pure crystallised bisphenol A is its low-foaming to foam-free dissolution to form sodium bisphenolate solutions (NaBPA), which are used in large quantities as a starting material in the production of polycarbonates. This means that NaBPA solutions which contain distilled bisphenol A have a lower surface activity, that is, a higher surface tension. The foaming activity of these solutions, which occurs industrially in essential inerting processes, transporting processes (pumping processes or storage in tanks and pipelines) and processing operations (reaction conditions in the reactor) is markedly reduced. Stable emulsions are thereby prevented. Moreover, highly pure crystallised bisphenols (99.90%–99.98% p,p-BPA) do not attain the extremely high surface tension values of distilled, highly pure bisphenols in NaBPA solutions.

Furthermore, the procedures hitherto required in the process for the filtration of the BPA melt are avoided by the removal at the bottom of the column. (Removal of metal powders containing Fe, Ni, Cr). Since bisphenol A is distilled over in one operation (two-column mode of operation: column 1), no further microparticles are to be found in the p,p-BPA melt.

The analysis and assessment of the distillation yields the following picture: very few isomers capable of rearrangement, such as o,p-BPA or alkylphenols, are formed during the distillation. High-boiling components are decomposed in fayour of o,p-BPA, phenol, alkylphenols. The loss of p,p-BPA over the entire process is less than 0.1%.

The bisphenol A purified by distillation according to the invention can be stored at temperatures of greater than 160° C. and is stable over long periods. It can therefore be stored in liquid form and is transportable. It can be used directly without previous cooling for the preparation of other polymers, for example, polycarbonate, polyimides, polyesters, polyacrylates, polysulphones, polyether ketones, block copolymers, copolymers etc.

EXAMPLES

Laboratory Distillation of Bisphenol A
(Discontinuous Tests)

Experimental conditions for discontinuous laboratory tests

The tests were carried out in a double-jacketed glass column 1.2 m in length (internal diameter 50 mm), 0.5 m filled with glass rings having d=10 mm. The distillation head used was a gas separator or liquid separator, which was modified for the condensation of low-boiling components. The low-boiling components were immobilised by cooling with water approximately 200 mm above the discharge point. The condensation of the distillates was carried out at 160° C. using glycerol.

As a rule the distillation was conducted at a pressure of approximately 0.5 mbar, measured at the outlet of the column. The temperature in the top of the column at the discharge point was 200° C.; the vapour-pressure curve of bisphenol A is taken as the basis (see Appendix 1), this signifies a pressure of approximately 1.5 mbar. The reflux ratio was adjusted to 1.5:1 (distillation time: less than 8 hours). The input of energy was carried out by jacket heating of the bottom of the column. The entire apparatus was first of all made thoroughly inert using nitrogen. During the distillation, nitrogen was blown in continuously through a capillary.

Method used for the discontinuous laboratory tests

To carry out the fractional distillation of the BPA melt, BPA flakes (for example, initial purity 99.72% p,p-BPA content) were distilled in an apparatus having a conventional gas-separator head.

At a reflux ratio of 2:1 and a pressure of from 1 to 1.5 mbar two first runnings of approximately 10% and 20% were taken; approximately 50% was isolated as the main fraction having a p,p-BPA content of from 99.95% to 99.96%.

A better quality of distillate could not be obtained using a gas separator; low-boiling components and the dimer of isopropylidenephenol could not be adequately immobilised in the top of the column and entered the distillate.

Considerably improved results were obtained using a modified liquid separator, which was equipped with a water cooler above the top of the column. The BPA flakes used (purity 99.80% p,p-BPA) were distilled at a reflux ratio of 1.5:1.

Under these conditions and after withdrawal of approximately 30% of first runnings, a fraction (44%) was isolated having a purity of 99.985% p,p-BPA content (method of determination: gas chromatographic notch ASTM method). The impurities were quantified as 10 ppm phenol, 40 ppm alkylphenols, 50 ppm chromanes and 50 ppm p,p-Me-BPA. Low-boiling components and o,p-BPA were removed in the first runnings, the high-boiling components trisphenol and Mol 402 remained completely behind in the bottom of the column.

The weight distribution in the first distillation of the liquid, after optimalisation, was as follows: first runnings 10.6% and 22%, main fraction 49.2%; distillate at the top of the column 7.1%; column hold up: 0.8, bottom: 9% and losses via the vacuum system 1.3%.

The analysis revealed a p,p-BPA loss of less than 1%.

Thermocolour stability of distilled BPA melt [by the Bagno test]

The main fractions were tested for their thermocolour stability by means of the Bagno Test (166° C. 90 min). All fractions showed Hazen colour indices of 5 and less than 5.

Bagno test 150 g of p,p-BPA (solid) is heated for 1.5 hours in a non-inert glass tube in a thermostatically-controlled oil bath maintained at 160° C. The glass tube is open at the top (opening) and freely aerated. After 1.5 hours the colour of the melted BPA is measured on the Hazen scale. Comparison tests are always carried out in parallel on other BPA flakes.

Colour test on BPA flakes

Distilled BPA flakes were tested in comparison with standard BPA flakes (BPA purities of 99.63% to 99.92% p,p-BPA) The BPA flakes were exposed continuously to an atmosphere of pure oxygen for 96 hours (500 ml glass flask, 150 g of BPA flakes, approximately 100 ml/h continuously. Current of $O_2$, daylight). Depending on the purity of the BPA and the effect of time and daylight, when compared visually a more or less distinct yellowing is observed in all the BPA flakes. The distilled BPA material showed no yellowing even after 96 hours.

Measuring of the surface tension/foam test using an NaBPA solution (Distilled BPA, crystalline BPA, conventional BPA in comparison)

The surface tension was determined by the drop-weight method. BPA flakes were introduced into a 14.5% NaBPA solution containing an excess of hydroxide of 0.2% (standard established in-house) and dissolved. Bisphenol A flakes, conventional bisphenols, recrystallised bisphenols and distilled bisphenol were tested under identical conditions using the foam test. Distilled, highly pure BPA showed the highest values for the surface tension and the lowest values in the determination of foam height.

Continuous tests on BPA distillation (continuous distillation)

By means of a continuous, two-stage distillation, bisphenol A purities of 99.98% to 99.99% p,p-BPA were obtained (Hazen less than 5).

Experimental adjustments

First column

Inflow: 400 ml/h; R/E: 0.5; withdrawal of bottoms: 20 ml/h; Düschi heater: 250° C.

Second column

R/E: 10; withdrawal of bottoms: 360 ml/h; distillate 20 ml/h; Düschi heater: 240° C.

The distillation was carried out at an operating pressure of from 2 mbar to 3 mbar (202° C. to 210° C.). The product feed lines are heated to 160° C., the internal temperatures of the column are also 160° C. The adiabatic jacket was reduced to 165° C. from 250° C. for preheating. The container for the melt (distillation receiver) has a temperature of 200° C. The BPA charge was flushed with nitrogen and evacuated prior to being pumped into the first column. When the receiver is refilled a pool of liquid should be present.

We claim:

1. A method for the preparation of ultra-pure bisphenol A by distillation, wherein:
   a) a bisphenol A melt is distilled;
   b) the distillation of the melt is carried out without the addition of stabilizers and under inert conditions;
   c) the distillation is carried out such that the losses through decomposition of p,p-bisphenol A are less than 0.5%;
   d) the distillation is carried out at temperatures of from 220° C. to 250° C.;
   e) the distillation is carried out under vacuum at 1 to 50 mbar;
   f) the distillation takes place in a first stage and a second stage,
   g) wherein in the first stage
      g.1) high-boiling components are removed;
      g.2) metal dust, metal ions and traces of salt, traces of acid, polymeric and oligomeric residues of catalysts and other non-distillable higher molecular compounds are removed;
      g.3) surface-active compounds are removed;
      g.4) low-boiling components and sulphur-containing low-boiling components are removed or reduced;
      g.5) concentrated BPA melt solutions containing low-boiling components, phenol and high-boiling components and having a p,p-bisphenol A content of greater than 92% are returned to the process as recycled streams;
   h) not more than 5% of concentrated BPA melt solutions containing low-boiling components and not more than 10% of concentrated BPA melt solutions containing high-boiling components are channelled into the process;
   i) low-boiling and high-boiling components contained in the channelled products mixed with p,p-BPA are returned to the process from the recycled streams, rearranged and partially recovered; and
   j) distilled p,p-bisphenol A is worked up as a stable bottom product free of other substances.

2. The method of claim 1, wherein the bisphenol melt (a) is produced by melting flakes, powder or pellets of bisphenol A having a p,p-bisphenol A content of at least 90% and a phenol content less than 10%.

* * * * *